US008071715B2

(12) United States Patent
Hurd et al.

(10) Patent No.: US 8,071,715 B2
(45) Date of Patent: Dec. 6, 2011

(54) MALEATED AND OXIDIZED FATTY ACIDS

(75) Inventors: Phillip W. Hurd, Conyers, GA (US); Gary D. Fultz, Spring, TX (US); Brett A Neumann, Covington, GA (US)

(73) Assignee: Georgia-Pacific Chemicals LLC, Atlanta, GA (US)

( * ) Notice: Subject to any disclaimer, the term of this patent is extended or adjusted under 35 U.S.C. 154(b) by 771 days.

(21) Appl. No.: 11/669,713

(22) Filed: Jan. 31, 2007

(65) Prior Publication Data

US 2008/0179570 A1 Jul. 31, 2008

(51) Int. Cl.
*C09F 7/00* (2006.01)
*C11D 15/00* (2006.01)
*C11D 3/02* (2006.01)
*B01D 12/00* (2006.01)
*B01F 17/00* (2006.01)

(52) U.S. Cl. .................. 530/230; 510/401; 516/204
(58) Field of Classification Search .................. 530/230; 510/401; 516/204
See application file for complete search history.

(56) References Cited

U.S. PATENT DOCUMENTS

| | | | |
|---|---|---|---|
| 2,039,243 A * | 4/1936 | Krzikalla et al. ............. 530/214 |
| 2,551,436 A | 5/1951 | Hampton |
| 2,554,487 A | 5/1951 | Breslow |
| 2,569,404 A | 9/1951 | Dazzi |
| 2,569,405 A | 9/1951 | Dazzi |
| 2,569,406 A | 9/1951 | Dazzi |
| 2,569,407 A | 9/1951 | Dazzi |
| 2,569,420 A | 9/1951 | Kosmin |
| 2,598,634 A | 5/1952 | Dazzi |
| 2,627,514 A * | 2/1953 | Kirkpatrick et al. .......... 530/231 |
| 2,628,226 A | 2/1953 | Lawrence |
| 2,630,418 A | 3/1953 | Dazzi |
| 2,661,359 A | 12/1953 | Dazzi |
| 2,756,210 A | 7/1956 | Raifsnider |
| 2,776,277 A | 1/1957 | Keim |
| 3,043,786 A * | 7/1962 | White .................. 521/43.5 |
| 3,106,550 A | 10/1963 | Bitting et al. |
| 3,112,209 A * | 11/1963 | Bradley, Jr. .................. 106/223 |
| 3,251,791 A * | 5/1966 | Goodchild ................. 525/501.5 |
| 3,278,562 A * | 10/1966 | Schnizer et al. ............. 549/528 |
| 3,341,485 A * | 9/1967 | Long ............................ 106/252 |
| 3,390,046 A | 6/1968 | McDavid |
| 3,497,490 A | 2/1970 | Arlt et al. |
| 3,522,279 A * | 7/1970 | Schnizer et al. ............. 549/272 |
| 3,632,822 A * | 1/1972 | Conroy ........................ 530/230 |
| 3,732,263 A * | 5/1973 | Berman ....................... 562/509 |
| 3,776,866 A | 12/1973 | Nakayama |
| 3,855,163 A * | 12/1974 | Bussell ........................ 530/230 |
| 3,919,453 A | 11/1975 | Bussell |
| 3,929,634 A | 12/1975 | Schuller |
| 3,931,336 A | 1/1976 | Schneider |
| 4,111,871 A * | 9/1978 | Aritomi ........................ 525/7.1 |
| 4,133,822 A * | 1/1979 | Hasman ....................... 530/230 |
| 4,207,231 A * | 6/1980 | Goodrich ..................... 524/705 |
| 4,218,851 A | 8/1980 | Roe |
| 4,233,162 A | 11/1980 | Carney |
| 4,292,221 A * | 9/1981 | Malatesta ..................... 524/313 |
| 4,312,631 A | 1/1982 | Cuntze et al. |
| 4,317,740 A | 3/1982 | Eisenhard |
| 4,337,193 A * | 6/1982 | Szita ............................ 527/105 |
| 4,410,431 A | 10/1983 | Roe |
| 4,415,337 A | 11/1983 | Kutta et al. |
| 4,447,344 A | 5/1984 | Roe |
| 4,511,366 A * | 4/1985 | Burrows et al. .................. 44/331 |
| 4,521,219 A * | 6/1985 | Perilstein ........................ 44/404 |
| 4,528,107 A | 7/1985 | McCaffrey et al. |
| 4,547,224 A | 10/1985 | Schilling |
| 4,614,235 A | 9/1986 | Keener et al. |
| 4,614,600 A | 9/1986 | Schilling et al. |
| 4,618,539 A * | 10/1986 | Jahnke et al. .................. 428/470 |
| 4,658,036 A | 4/1987 | Schilling |
| 4,751,025 A | 6/1988 | Olechowski et al. |
| 4,770,766 A | 9/1988 | Keller, Jr. et al. |
| 4,927,669 A | 5/1990 | Knox et al. |
| 4,957,511 A | 9/1990 | Ljusberg-Wahren |
| 5,147,528 A | 9/1992 | Bulatovic |
| 5,182,326 A | 1/1993 | LeBlanc et al. |
| 5,292,480 A | 3/1994 | Fischer et al. |
| 5,300,569 A | 4/1994 | Drake et al. |
| 5,328,505 A | 7/1994 | Schilling |
| 5,338,347 A * | 8/1994 | Rohr et al. .................. 106/14.44 |
| 5,344,483 A * | 9/1994 | Hinton ........................ 106/31.35 |
| 5,348,676 A * | 9/1994 | Takashima et al. ........... 508/216 |
| 5,379,902 A | 1/1995 | Wen et al. |
| 5,385,616 A | 1/1995 | Dougherty et al. |
| 5,407,471 A * | 4/1995 | Rohr et al. .................. 106/14.44 |
| 5,420,317 A * | 5/1995 | Laufenberg et al. .......... 554/163 |

(Continued)

FOREIGN PATENT DOCUMENTS

CA 2299857 9/2003

(Continued)

OTHER PUBLICATIONS

Machine Translation of DE 10015913 A1, 2010.*
Shigeno et al., trans-Stereoisomer of adducts of maleic anhydride with olefinic unsaturated fatty acids, Kogyo Kagaku Zasshi, 1957, pp. 577-582, vol. 60.
Shigeno et al., Derivatives of maleinated monoolefinic unsaturated fatty acids as synthetic lubricants and oiliness improver, Kogyo Kagaku Zasshi, 1957, pp. 582-586, vol. 60.
Shigeno et al., Derivatives of maleinated monoolefinic unsaturated fatty acids and their utilization as rust inhibitor, antibacterial agent, surface-active agent, and stabilizer for poly(vinyl chloride) resin, Kogyo Kagaku Zasshi, 1957, pp. 720-728, vol. 60.
Volodkovich et al., Organic insectofungicides. XXXV. Reaction of 1,1-difluorotetrachlorocyclopentadiene with some unsaturated compounds, Zhurnal Obshchei Khimmii, Oct. 1958, pp. 3153-3156, vol. 28—issue 10, Consultants Bureau Inc, New York, United States of America (English Translation).

(Continued)

Primary Examiner — Liam Heincer
(74) Attorney, Agent, or Firm — Michael S. Kerns

(57) ABSTRACT

An oxidized and maleated fatty acid composition, especially an oxidized and maleated tall oil fatty acid-containing product useful in formulating corrosion inhibitors and for use as an emulsifier, especially for petroleum-related applications.

13 Claims, No Drawings

U.S. PATENT DOCUMENTS

| | | | |
|---|---|---|---|
| 5,443,158 A | 8/1995 | McKenny et al. | |
| 5,481,025 A * | 1/1996 | Laufenberg et al. | 554/142 |
| 5,556,451 A | 9/1996 | Minevski | |
| 5,582,792 A | 12/1996 | Dougherty et al. | |
| 5,643,534 A | 7/1997 | Minevski | |
| 5,658,860 A | 8/1997 | Clark et al. | |
| 5,670,056 A | 9/1997 | Yoon et al. | |
| 5,698,668 A * | 12/1997 | Bender | 530/200 |
| 5,704,961 A | 1/1998 | Hudson | |
| 5,759,485 A | 6/1998 | Fischer et al. | |
| 5,795,376 A * | 8/1998 | Ide | 106/31.73 |
| 5,864,049 A | 1/1999 | Dos Santos et al. | |
| 5,869,433 A | 2/1999 | Patel | |
| 5,929,408 A | 7/1999 | Gutierrez et al. | |
| 5,977,037 A | 11/1999 | Giret et al. | |
| 6,145,667 A | 11/2000 | Rothenberg et al. | |
| 6,149,013 A | 11/2000 | Hughes | |
| 6,153,693 A * | 11/2000 | Matzinger et al. | 525/54.42 |
| 6,170,669 B1 | 1/2001 | Senior et al. | |
| 6,200,377 B1 | 3/2001 | Basilio et al. | |
| 6,341,697 B1 | 1/2002 | Miller et al. | |
| 6,375,853 B1 | 4/2002 | Yoon | |
| 6,409,022 B1 | 6/2002 | Rothenberg et al. | |
| 6,426,321 B1 | 7/2002 | Durrieu et al. | |
| 6,469,125 B1 * | 10/2002 | Fontana et al. | 528/158.5 |
| 6,526,675 B1 | 3/2003 | Yoon | |
| 6,583,263 B2 | 6/2003 | Gaudl | |
| 6,589,917 B2 | 7/2003 | Patel et al. | |
| 6,620,770 B1 | 9/2003 | Kirsner et al. | |
| 6,666,268 B2 | 12/2003 | Griffith et al. | |
| 6,668,929 B2 | 12/2003 | Griffith et al. | |
| 6,774,094 B2 | 8/2004 | Jovancicevic et al. | |
| 6,793,079 B2 | 9/2004 | Khan et al. | |
| 6,799,682 B1 | 10/2004 | Yoon | |
| 6,800,594 B2 | 10/2004 | Miksic et al. | |
| 6,849,581 B1 | 2/2005 | Thompson et al. | |
| 6,871,743 B2 | 3/2005 | Yoon | |
| 6,988,623 B2 | 1/2006 | Magliocco et al. | |
| 7,008,907 B2 | 3/2006 | Kirsner et al. | |
| 7,137,401 B2 | 11/2006 | Jovancicevic et al. | |
| 7,137,407 B2 | 11/2006 | Jovancicevic et al. | |
| 7,479,184 B1 * | 1/2009 | Dehuvyne et al. | 106/218 |
| 2003/0116065 A1 | 6/2003 | Griffith et al. | |
| 2003/0130135 A1 | 7/2003 | Hou et al. | |
| 2004/0144957 A1 | 7/2004 | Miksic et al. | |
| 2004/0171498 A1 | 9/2004 | Miller | |
| 2005/0080178 A1 | 4/2005 | Fujii et al. | |
| 2005/0137093 A1 | 6/2005 | Miller | |
| 2007/0075120 A1 * | 4/2007 | Yang et al. | 228/101 |
| 2007/0167333 A1 * | 7/2007 | Hurd et al. | 507/244 |
| 2008/0179570 A1 * | 7/2008 | Hurd et al. | 252/396 |
| 2008/0194795 A1 | 8/2008 | Hurd et al. | |
| 2008/0272342 A1 | 11/2008 | Guzmann et al. | |
| 2008/0305531 A1 * | 12/2008 | Lam et al. | 435/142 |
| 2009/0065736 A1 * | 3/2009 | Johnson et al. | 252/88.1 |
| 2009/0194466 A1 * | 8/2009 | Hines et al. | 209/166 |
| 2009/0194731 A1 | 8/2009 | Hurd et al. | |
| 2010/0028272 A1 | 2/2010 | Knappe et al. | |

FOREIGN PATENT DOCUMENTS

| | | |
|---|---|---|
| DE | 10015913 A1 * | 10/2000 |
| EP | 0239770 | 9/1989 |
| EP | 711850 | 5/1996 |
| EP | 1676897 A1 | 7/2006 |
| JP | 18020 | 9/1949 |
| JP | 30-8548 B | 11/1955 |
| JP | 32-331 B4 | 1/1957 |
| JP | 60-018583 A | 1/1985 |
| WO | 89/11516 A1 | 11/1989 |
| WO | WO 00/52230 | 9/2000 |
| WO | WO 2004/050801 A1 | 6/2004 |
| WO | 2007/002558 A1 | 1/2007 |

OTHER PUBLICATIONS

Eslami, Addition products of maleic anhydride with oleic acid and some of their derivatives, Journal des Recherches du Centre National de la Recherche Scientifique, Dec. 1962, pp. 333-355, No. 61, Paris, France.

Izumi et al., Fatty acid derivatives and their utilization. IX. Synthesis and properties of high-molecular-weight aliphatic poly (amide-amines), Kogyo Kagaku Zasshi, Apr. 1969, pp. 1018-1022, vol. 72—issue 4.

Novakov et al., Sythesis and properties of some epoxy esters and water-borne coatings prepared on their basis, Surface Coatings International, Mar. 1993, pp. 111-115, vol. 76—No. 3, Oil and Colour Chemists' Association, Wembley, England.

Isogai et al., Emulsion stability and sizing performance of alkyl oleate-succinic anhydrides, Paper Technology, Sep. 2004, pp. 19-24, vol. 45—No. 7, PITA, Bury, Lancs, England.

PCT International Search Report and Written Opinion of the International Searching Authority for PCT/US2008/052682 mailed Dec. 10, 2008.

Novakov, P., Iliev, I., and Patrenko, P., "Synthesis and Properties of Some Epoxy Esters and Water-borne Coatings Prepared on Their Basis", PRA Conference on Developments in New Technology and Marketing Opportunities in East and West Europe, Nov. 18-19, 1992, Brussels.

SciFinder Search Results for "Maleated Tall Oil, Oxidized." Search conducted Aug. 25, 2006 yielding 4 references. pp. 1-3.

SciFinder Search Results for "Oxidized Maleated Tall Oil." Search conducted Aug. 25, 2006 yielding 4 references. pp. 1-3.

Specification for Tall Oil Products-Product Information "XTOL® 690 Modified Tall Oil." 1996, 2002 Georgia-Pacific Resins, Inc.

Specification for Tall Oil Products-Product Information "Latol MTO® Oxidized Tall Oil." 1996, 2002 Georgia-Pacific Resins, Inc.

Specification for Tall Oil Products-Product Information "XTOL® 304 Tall Oil Fatty Acid." 1996, 2002, 2007 Georgia-Pacific Chemicals LLC.

Specification for Tall Oil Products-Product Information "XTOL® 100 Tall Oil Fatty Acid." 1996, 2002, 2007 Georgia-Pacific Chemicals LLC.

Specification for Tall Oil Products-Product Information "XTOL® 101 Tall Oil Fatty Acid." 1996, 2002, 2007 Georgia-Pacific Chemicals LLC.

Specification for Tall Oil Products-Product Information "XTOL® 300 Tall Oil Fatty Acid." 1996, 2002, 2007 Georgia-Pacific Chemicals LLC.

Specification for Tall Oil Products-Product Information "XTOL® 531 Distilled Tall Oil." 1996, 2002 Georgia-Pacific Resins, Inc.

Material Safety Data Sheet—"XTOL® 692 Modified Tall Oil." pp. 1-6. Effective Date May 23, 2005. Georgia Pacific Chemicals LLC.

Babkina, M.M. et al., "Alkyl Resins Made from Tall Oil and Maleic Anhydride", Depositied Doc. (1980), 12 pp.

G.F. Filippychev et al., Khim. Him. Teckhnol., 1973, 25-27 Novakov, P. et al., Surface Coatings International, 76 (3): 111-115(1993)—Abstract only.

Material Safety Data Sheet—"XTOL® 0530 Rosin Fortified Distilled Tall Oil", pp. 1-6, Effective Date Oct. 30, 1997, Georgia Pacific Chemicals LLC.

Material Safety Data Sheet—"LYTOR® 100 Tall Oil Rosin", pp. 1-7, Effective Date Jan. 22, 2001, Georgia-Pacific Chemicals LLC.

Material Safety Data Sheet—"LYTOR® 101 Tall Oil Rosin", pp. 1-7, Effective Date Jan. 22, 2001, Georgia-Pacific Chemicals LLC.

Material Safety Data Sheet—"XTOL® 0520 Distilled Tall Oil", pp. 1-7, Effective Date Dec. 9, 2004, Georgia-Pacific Chemicals LLC.

Material Safety Data Sheet—"XTOL® MTO Modified Tall Oil", pp. 1-7, Effective Date May 23, 2007, Georgia-Pacific Chemicals LLC.

Material Safety Data Sheet—"XTOL® 0542 Rosin Fortified Distilled Tall Oil", pp. 1-7, Effective Date Oct. 9, 2007, Georgia-Pacific Chemicals LLC.

Material Safety Data Sheet—"XTOL® 692 Modified Tall Oil", pp. 1-7, Effective Date Oct. 30, 2007, Georgia-Pacific Chemicals LLC.

Material Safety Data Sheet—"XTOL® 690 Modified Tall Oil", pp. 1-7, Effective Date Jan. 23, 2008, Georgia-Pacific Chemicals LLC.

Material Safety Data Sheet—"XTOL® 304 Tall Oil Fatty Acids", pp. 1-6, Effective Date Apr. 4, 2008, Georgia-Pacific Chemicals LLC.

Material Safety Data Sheet—"XTOL® 100 Tall Oil Fatty Acids", pp. 1-6, Effective Date Apr. 14, 2008, Georgia-Pacific Chemicals LLC.

Material Safety Data Sheet—"XTOL® 101 Tall Oil Fatty Acids", pp. 1-6, Effective Date Apr. 14, 2008, Georgia-Pacific Chemicals LLC.

Material Safety Data Sheet—"XTOL® 300 Tall Oil Fatty Acids", pp. 1-6, Effective Date Apr. 14, 2008, Georgia-Pacific Chemicals LLC.

Huntsman Corporation, Technical Bulletin for "JEFFAMINE® D-230 amine Epoxy Curing Agent", 1 page, 2005, 2006.

Huntsman Corporation, Technical Bulletin for "JEFFAMINE® D-400 Polyetheramine", 2 pages, 2007, 2008.

Huntsman Corporation, Technical Bulletin for "JEFFAMINE® D-2000 Polyetheramine", 2 pages, 2007, 2008.

Kantro, D.L. "Influence of Water-Reducing Admixtures on Properties of Cement Paste—A Miniature Slump Test", Cement, Concrete, and Aggregates, vol. 2, No. 2, Winter 1980, pp. 95-102, ASTM International.

Shi, et al., Functionalization of Isotactic Polyproplylene with Maleic Anhydride by Reactive Extrusion: Mechanism of Melt Grating, Polymer, vol. 42, 2001, pp. 5549-5557. Elsevier Science Limited.

International Search and Written Opinion of the International Search Authority for PCT/US2009/032701 mailed May 20, 2009.

Office Actions for U.S. Appl. No. 12/023,886.

Office Actions for U.S. Appl. No. 12/363,483.

\* cited by examiner

MALEATED AND OXIDIZED FATTY ACIDS

FIELD OF THE INVENTION

The present invention relates to an oxidized and maleated fatty acid-containing product. The present invention particularly relates to an oxidized and maleated tall oil fatty acid-containing product. Such products are useful in formulating corrosion inhibitors and as an emulsifier, especially for petroleum-related applications.

BACKGROUND OF THE INVENTION

Catalytic (thermal) polymerization of tall oil fatty acids produces a product known as dimer/trimer acid which the oil industry has traditionally employed as an oil-soluble corrosion inhibitor for reducing corrosion in oil well piping and related recovery equipment. The thermal polymerization causes the $C_{18}$ tall oil fatty acids (containing one or two double bonds, e.g. oleic and linoleic acids, respectively), in the presence of a suitable catalyst, to give varying amounts of $C_{36}$ (dimerized) and $C_{54}$ (trimerized) fatty acids. These dimer and/or trimer fatty acids may be neutralized with an appropriate amine, such as diethylenetriamine, to produce a corrosion inhibitor. The dimer/trimer acid-based product is said to inhibit corrosion by coating metal surfaces with a thin film, thereby excluding the water necessary for corrosion processes to occur.

Over the years, the corrosion inhibition art has looked for alternatives to the dimer/trimer acid-based product. Of particular interest in this regard is the class of fatty acid-based products which have been functionalized with maleic anhydride and/or fumaric acid.

Thus, according to U.S. Pat. No. 4,927,669, tall oil fatty acid (TOFA) is functionalized using maleic anhydride, or fumaric acid, in the presence of a catalyst such as iodine, clay or silica. The fatty acids are reacted in a first step to promote a Diels-Alder reaction with linoleic acid, the product then being distilled to remove unreacted fatty acid. In a second step, non-conjugated acid, e.g., oleic/elaidic acids, are treated under more vigorous conditions to form an ene adduct. Residual unreacted fatty acid is removed. The product is said to contain 75 to 95% maleinized fatty acids, 15 to 20% thermal dimer and trimer and unreacted fatty acid and is useful as a corrosion inhibitor.

U.S. Pat. No. 5,292,480 condenses the maleic anhydride-functionalized TOFA of U.S. Pat. No. 4,927,669 with a polyalcohol, such as ethylene glycol, diethylene glycol, triethylene glycol, polyethylene glycol, glycerin, pentaerythritol, trimethylolpentane, and sorbitol to form an acid-anhydride ester corrosion inhibitor, which in turn may be neutralized with an amine, with a metal oxide, or with a hydroxide before use. U.S. Pat. No. 5,385,616 is similar in describing the reaction product of the maleic anhydride-functionalized TOFA of U.S. Pat. No. 4,927,669 and an alcohol (ROH).

In U.S. Pat. No. 5,582,792, the maleic anhydride-functionalized TOFA is esterified (as in U.S. Pat. No. 5,385,616 and then is reacted with an ethoxylated amine, such as an ethoxylated fatty amine. The composition is useful for corrosion inhibition.

U.S. Pat. No. 5,759,485 describes a class of water soluble corrosion inhibitors in which the maleic anhydride-functionalized TOFA (specifically the Diels-Alder reaction adduct with linoleic acid) is neutralized with aminoethylethanolamine and also with one of imidazoline, amidoamine or a combination thereof. Canadian Pat. 2,299,857 describes a similar corrosion inhibitor made by reacting (neutralizing) maleated TOFA with alkanolamines.

As evidenced by the foregoing prior art attempts to develop corrosion inhibitors based on maleated TOFA, those skilled in the art continue to explore new techniques and compositions for using tall oil-related raw materials in manufacturing new corrosion inhibitors and other products.

DETAILED DESCRIPTION OF THE INVENTION

The present invention relates to methods for preparing a composition suitable for a variety of uses, which methods involve the combination of both maleating and oxidizing a fatty acid material, particularly a tall oil fatty acid-containing material. The composition so-prepared is useful as an emulsifier in making petroleum-related products, such as invert water-in-oil emulsions used as drilling muds and is useful as a corrosion inhibitor for metal surfaces, especially in oil well applications. The present invention also relates to the resulting composition produced by such methods and the use of the composition in such applications.

The oxidized and maleated fatty acid-containing compositions, especially the oxidized and maleated tall oil compositions and particularly the oxidized and maleated tall oil fatty acid (TOFA) compositions of the present invention can successfully protect metals in a way which reduces their corrosion when exposed to a corrosive environment, such as water.

The oxidation and the maleation (with maleic anhydride and/or fumaric acid and/or (meth)acrylic acid) of the fatty acid materials and particularly the tall oil materials can be conducted in either order. The fatty acids, such as a tall oil product and particularly TOFA, can first be maleated and then the maleation can be followed by an oxidation. Alternatively, the fatty acid material can first be oxidized and then the oxidized fatty acid product can be maleated.

As used throughout the specification and in the claims the terms maleated, maleation and the like refer to the modification of unsaturated fatty acid molecules, especially unsaturated rosin acids and $C_{18}$-fatty acids, such as linoleic acid, and oleic acid, which introduces additional carboxylic moieties onto the molecules by reaction with one or more of maleic anhydride, fumaric acid, acrylic acid and methacrylic acid (hereafter acrylic acid and methacrylic acid are generally referred to in the aggregate or alternative as (meth)acrylic acid). Use of maleic anhydride is generally preferred.

While the present invention is broadly directed to the modification of a variety of unsaturated fatty acid materials by the combination of oxidation and maleation, the invention is particularly aimed at modifying tall oil products containing such unsaturated fatty acids.

In contrast to the prior art, where there apparently has been a concerted effort to use tall oil materials containing primarily, if not almost exclusively, tall oil fatty acids (TOFA) and to conduct the reaction with maleic anhydride (and/or with fumaric acid and/or acrylic acid) in a way to promote the formation of the Diels-Alder reaction adduct with linoleic acid (generally by using a catalyst), the present inventors have found such restrictions are not necessary.

In particular, the inventors have found that suitable products for use as emulsifiers and corrosion inhibitors can be made using a variety of tall oil products that contain unsaturated fatty acids including crude tall oil, i.e., tall oil that contains both rosin acids and fatty acids, blended tall oil products containing both rosin acids and fatty acids, distilled tall oil products and tall oil fatty acid (TOFA).

In addition, in practicing the present invention there is no need to focus on the production of the Diels-Alder reaction adduct with conjugated fatty acids, such as linoleic acid. Thus, the conditions under which the maleation is conducted do not need to be controlled (e.g., a catalyst is not needed) such that the Diels-Alder reaction predominates.

Representative structures present in oxidized and maleated tall oil compositions of the present invention would thus include the following molecular species:

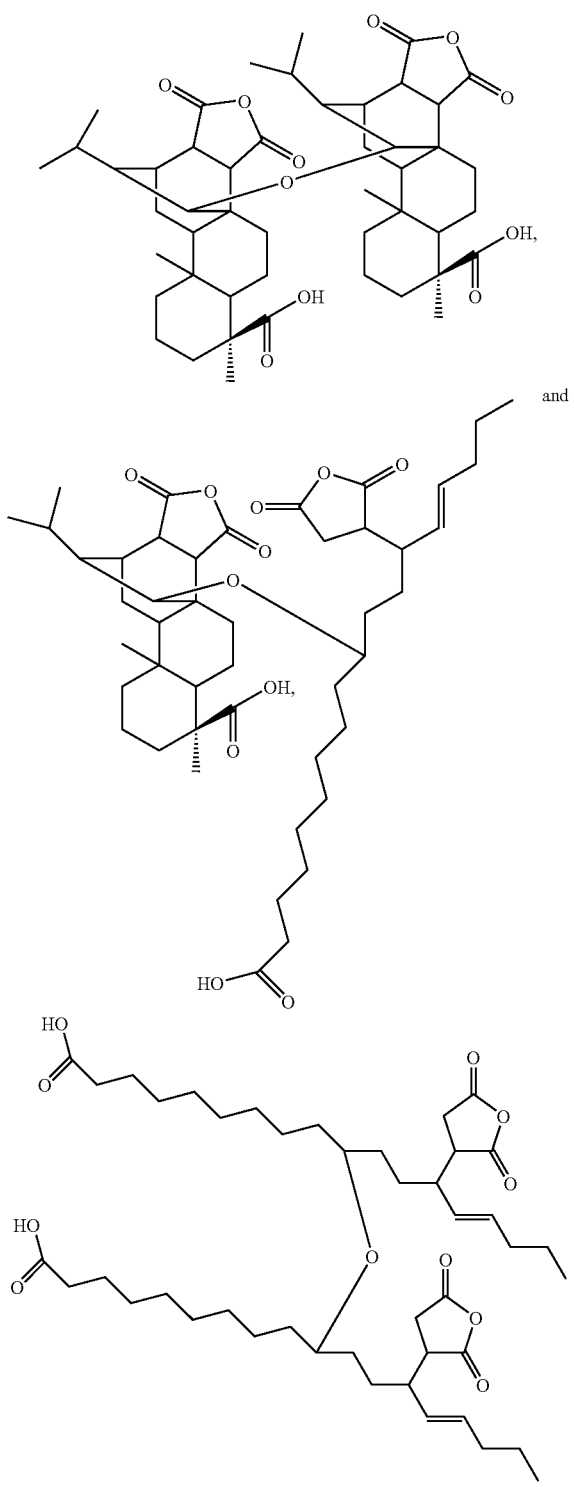

As will be appreciated by those skilled in the art from these representative molecules, such structures have a higher carboxylic functionality than dimer/trimer acids at similar molecular weights. This higher carboxylic function enhances the salt or soap formation of the compositions (important to their use as emulsification aides) and gives the compositions a stronger film persistency on metal surfaces.

As a general rule, oils containing a significant amount of $C_{18}$ unsaturated fatty acids should be suitable as sources of the fatty acid-containing starting materials for the present method. As a representative, though not an exclusive or exhaustive list of possible oils that can be used as a source of unsaturated fatty acids for preparing an oxidized and maleated fatty acid-containing composition in connection with the preparation of a composition of the present invention can be mentioned the following: linseed (flaxseed) oil, castor oil, tung oil, soybean oil, cottonseed oil, olive oil, canola oil, corn oil, sunflower seed oil, coconut oil, safflower oil, tall oil, palm oil and mixtures thereof. It may also be suitable in some cases to use the distillation products of such oils or their distillation residues. In this regard, specific mention can be made of distilled tall oil and tall oil bottoms. These oils contain as one significant constituent linoleic acid, an unsaturated (conjugated) long chain fatty acid as well as other unsaturated fatty acids, Fatty acids suitable for use in the present invention (found in such oils) have double bonds, i.e., sites of unsaturation in their hydrocarbon chains. As a result, such sources of fatty acids often are referred to as unsaturated oils. As well known to those skilled in the art, the fatty acids in these oils can be polymerized by heating them in the presence of oxygen or air. This polymerization typically causes an increase in the viscosity of the oxidized fatty acid material (oil). A catalyst is sometimes used to increase the speed of the oxidation reaction in order to reduce the time required to attain the desired level of oxidation and associated viscosity increase, or to reduce the temperature at which the oxidation is conducted. Use of such a catalyst is optional.

The oxidative heating treatment causes crosslinking of the hydrocarbon chains of the unsaturated fatty acid via their double bonds (sites of unsaturation), via an oxygen (ether) linkage The oxygenation treatment is continued until a desired result is obtained, such as a desired acid value, or a desired viscosity is reached in the treated fatty acid material. Those skilled in the art can readily obtain an oxidized fatty acid composition of a suitable acid value or viscosity.

Oxidized fatty acid materials suitable for use in the present invention are commercially available. In any event, in the case of a tall oil material, for example, the tall oil fatty acids in such materials can be oxidized by heating the tall oil material to a temperature above about 150° C., for example to a temperature in the range of 160° C. to 170° C., and then sparging oxygen or air through the heated tall oil material. As understood by those skilled in the art, a variety of techniques and devices can advantageously be used to inject the oxygen or air into the heated tall oil and the present invention is not limited to any specific technique or equipment. The oxidation reactions generally are continued until the desired acid value or viscosity is achieved in the tall oil, indicative that the desired level of cross-linking has been obtained in the oxidized tall oil material.

Use of a tall oil material is generally favored based on consideration of both its cost and performance. As is known in the art, tall oil refers to the resinous yellow-black oily liquid obtained as an acidified byproduct in the Kraft or sulfate processing of pine wood. Tall oil, prior to refining, is normally a mixture of rosin acids, fatty acids, sterols, high-molecular weight alcohols, and other alkyl chain materials. Distillation of crude tall oil is often used to recover a mixture of fatty acids in the C16-C20 range. The commercially available tall oil products XTOL®100, XTOL®300, and XTOL®304 (all from Georgia-Pacific Chemical LLC, Atlanta, Ga.), for examples all contain saturated and unsaturated fatty acids in the C16-C18 range, as well as minor amounts of rosin acids.

To prepare a maleated tall oil, a tall oil material, such as a tall oil distillate component is reacted with maleic anhydride (and/or fumaric acid and/or (meth)acrylic acid). Representative tall oil distillate components include tall oil fatty acids, tall oil rosin acids, and mixtures of these fractions. The refinement (i.e., fractionation) of tall oil can, for example, provide $C_{16}$-$C_{18}$ saturated and unsaturated fatty acids as well as fatty acid/rosin acid mixtures. In preparing maleated tall oil, such tall oil distillate components, lighter (i.e., lower boiling) or heavier (i e., higher boiling) components, or components having broader or narrower boiling point ranges may be used in the reaction with maleic anhydride (and/or fumaric acid and/or (meth)acrylic acid). Mixtures or blends of various tall oil distillate fractions may also be employed as the tall oil material. Fatty acid/rosin acid mixtures in a desired ratio may be obtained in a single distillate fraction by adjusting tall oil fractionation conditions. Representative tall oil distillate components include the previously mentioned, commercially available products XTOL®100, XTOL®300, and XTOL®304, and XTOL®530, and LYTOR®100 (all from Georgia-Pacific Chemical LLC, Atlanta, Ga.).

In one embodiment, for example, a mixture of a first tall oil distillate fraction comprising predominantly tall oil fatty acids (e.g., XTOL®100) and a second tall oil distillate fraction comprising predominantly rosin acids (e.g., LYTOR®100) may be blended in a wide range of proportions. In such mixtures, representative amounts of fatty acids and rosin acids range from about 45% to about 90% by weight and from about 10% to about 55% by weight, respectively. Representative weight ratios of the first tall oil distillate fraction to the second tall oil distillate fraction may range from about 3:2 to about 4:1. If such a blend is used to form a maleated tall oil material via reaction with maleic anhydride (and/or fumaric acid and/or (meth)acrylic acid), suitable amounts of the anhydride (or acid(s)) may range from about 2% to about 25% by weight, usually from about 2% to about 15% by weight, based on the combined weight of the tall oil fractions and the anhydride (or acid(s). Depending on the tall oil composition and fractionation conditions, a single tall oil distillate fraction may also suffice to yield a composition that is substantially the same as any of the blends of tall oil distillate factions discussed above.

In preparing a maleated tall oil from the reaction of a tall oil material, such as tall oil distillate components, and maleic anhydride and/or fumaric acid and or (meth)acrylic acid, i.e., one or more of maleic anhydride, fumaric acid and (meth) acrylic acid, a reaction temperature generally from about 150° C. (300° F.) to about 250° C. (480° F.), often from about 200° C. (390° F.) to about 230° C. (445° F.), and preferably from about 215° C. (420° F.) to about 225° C. (435° F.), is used. Use of a catalyst is generally optional, i.e. it is not needed. Catalysts that can optionally be used are known in the prior art. Some of the representative reactions that can occur are illustrated in U.S. Pat. No. 4,927,669.

Such maleated tall oil products can be obtained commercially as XTOL®690 and XTOL®692 (from Georgia-Pacific Chemical, LLC, Atlanta, Ga.).

In general, the maleation reactions are essentially complete after a reaction time from about 5 hours to about 36 hours, and typically from about 20 hours to about 30 hours. Without being bound by theory, the maleic anhydride (and/or fumaric acid and/or (meth)acrylic acid) reacts with the fatty acid material, such as the tall oil distillate components at various sites of unsaturation (i.e., carbon-carbon double bonds), present in the reactants. For example, the reaction of maleic anhydride with an unsaturated tall oil fatty acid results in the addition of the anhydride ring to the acid at olefinic sites via the so-called "ene" reaction. The reaction of maleic anhydride with a rosin acid derived from tall oil, at diolefinic sites and with conjugated fatty acids, may alternatively form a Diels-Alder addition product having a 6-membered ring with one site of unsaturation.

As noted above, the steps of oxidation and maleation of the fatty acid-containing material, and particularly a tall oil material, can be conducted in either order, as illustrated by the examples which follow. Also contemplated is the simultaneous oxidation and maleation of the fatty acid-containing material, and particularly a tall oil material.

For use in corrosion applications and especially for emulsion applications, applicants also contemplate that the oxidized and maleated tall oil material of the present invention can be combined with other materials such as alkyleneamines, including diethylenetriamine, imidazoline, amidoamine, amidoamine condensates, alkanolamines and the like.

When used in corrosion inhibition applications, the compositions of the present invention will normally be used in a concentration from about 5 ppm up to as much as 10% by weight, more usually in an amount between 20 ppm and 1% by weight. When used as an emulsifier, generally the oxidized and maleated fatty acid compositions, such as the oxidized and maleated tall oil material, will be used in an amount of from about 2% to about 15% by weight of the emulsion.

Also, the oxidized and maleated fatty acid compositions, such as the oxidized and maleated tall oil compositions of the present invention may be dissolved or dispersed in a carrier solvent to facilitate the coating of metals when used as a corrosion inhibiting composition. Suitable carrier solvents include, but are not limited to, the following: water, alcohols, kerosene, crude oil and combinations thereof.

In petroleum-recovery applications, where the present invention is usefully employed, the downhole conditions in an oil or gas well can vary greatly from one well to the next. That is, in one environment one may encounter "sweet" conditions (predominately $CO_2$) while in another environment "sour" conditions may predominate ($H_2S$ present). As shown in the following examples, the oxidized and maleated fatty acid compositions, such as in particular the oxidized and maleated tall oil compositions of the present invention are suitable for retarding corrosion in both environments.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

EXAMPLE 1

Oxidation of Maleated Tall Oil Products

A maleated tall oil product such as the commercially available XTOL®690 or XTOL®692 products is oxidized using air at an elevated temperature. XTOL®690 is a tall oil blend of tall oil fatty acid bottoms and a distilled tall oil, which blend has been maleated at a level of about 3.5%. XTOL®692 is a blend of a tall oil rosin and tall oil fatty acid, which blend has been maleated at a level of about 12%.

Each of these tall oil blends can be charged to a reactor which is fitted with an agitator, a thermocouple and a fritted glass sparge stone attached by a hose to an air supply. The tall oil blends are heated to 165° C. and the air turned on and adjusted to a flow rate of 4 L/hr through the sparge stone. The maleated tall oil reaction mixture is then heated to 177° C. and sampled frequently for acid value and viscosity (Gardner-Holdt) as the oxidation reactions proceed, while holding the reaction mixture at a temperature of 177° C. The reaction mixture is held at a temperature of 177° C. for 10.5-16 hours as air is sparged. The reaction mixture is then cooled to 70-85° C. and discharged. The final physical properties of the maleated and oxidized tall oil product can be determined. In one example, the properties of the maleated and oxidized tall oil products were measured as shown in the following table with reference to typical properties of the starting materials:

|  | XTOL ® 690 | Oxidized XTOL ® 690 | XTOL ® 692 | Oxidized XTOL ® 692 |
|---|---|---|---|---|
| Acid Value (mg KOH/g) | 197.3 | 158.7 | 276.0 | 203.9 |
| Brookfield Viscosity. (cPs; 25° C.) | 484.9 | 8496 | 1451 | 18010 |
| Density (Lbs./gal) | 8.00 | 8.38 | 8.41 | 8.59 |
| Sp. Gravity. (25° C.) | 0.961 | 1.006 | 1.010 | 1.031 |

EXAMPLE 2

Maleation of Oxidized Tall Oil

This example demonstrates the reverse of the process described in Example 1 for making a composition of the present invention, whereby one starts with an oxidized tall oil product and then proceeds with the maleation. In this example, a an oxidized tall oil product, LATOL®MTO, which is an oxidized, high acid value crude tall oil, available commercially from Georgia Pacific is used as the starting material. This oxidized crude tall oil is then treated with maleic anhydride.

LATOL®MTO (95 wt %) is charged to a sealed reactor fitted with an agitator, a thermocouple and a condenser. The reactor is heated to 180° C. At 180° C. maleic anhydride (5 wt %) is added slowly to the reactor. The reaction mixture is then heated to 200° C. for approximately 3-6 hours or until all of the maleic anhydride has reacted. The reaction mixture is then cooled to 70-80° C. and discharged. The final physical properties can be determined. In one example, the properties of the oxidized and maleated tall oil product were measured as shown in the following table with reference to typical properties of the starting materials:

|  | LATOL ® MTO | Maleated LATOL ® MTO (Oxidized tall oil) |
|---|---|---|
| Acid Value | 143.0 | 163.8 |
| Density (25° C.; Lbs/gal) | 8.25 | 8.52 |
| Sp. Gravity (25° C.) | 0.99 | 1.023 |
| Brookfield Viscosity. (cPs: 25° C.) | 4870 | 22580 |

EXAMPLE 3

Maleation of Crude Tall Oil Followed by Oxidation

This process is similar to the one described in Example 1 whereby one starts with a Crude Tall oil mixture, but maleates it to a level of about 5% and then proceeds with an oxidation of the maleated tall oil product.

A crude Tall Oil (95 wt. %) is charged to a sealed reactor fitted with an agitator, a thermocouple and a condenser. The reaction mixture is heated to 180° C. At 180° C., maleic anhydride (5 wt. %) is added slowly to the reactor. The reaction mixture is then heated to 200° C. for approximately 3-6 hours or until all of the maleic anhydride has reacted. Once all of the maleic anhydride has reacted, the reaction mixture is then cooled to 180° C. and air is introduced to the reaction mixture using a flitted glass sparge stone attached by a hose to an air supply. The air is turned on and adjusted to a flow rate of 4 L/hr through the sparge stone. Oxidation of the maleated crude tall oil with air is carried out for 12-16 hours. The reaction mixture is then cooled to 70-85° C. and discharged. The final physical properties can be determined. In one example, the properties of the maleated and oxidized tall oil product was measured as shown in the following table with reference to typical properties of the starting materials:

|  | Crude Tall Oil | Maleated-Oxidized Crude tall oil |
|---|---|---|
| Acid Value | 161.6 | 169.5 |
| Density (25° C.; Lbs/gal) | 8.088 | 8.54 |
| Specific. Gravity (25° C.) | 0.9706 | 1.027 |
| Brookfield Viscosity (cPs; 25° C.) | 695.0 | 33800 |

EXAMPLE 4

Oxidation of Maleated Tall Oil Fatty Acid

In this example, a maleated tall oil fatty acid (TOFA) was oxidized using air at an elevated temperature.

TOFA is charged to a scaled reactor and the contents of the reactor are heated to 70° C. Once a temperature of 70° C. is achieved maleic anhydride in an amount of about 25% by weight of th TOFA is added to the vessel. After all maleic anhydride is in the reactor the reactor mixture is heated to 220° C. in several stages. From the starting temperature of 70° C.; the temperature is increased in small increments until 220° C. is achieved. After each temperature adjustment and the desired set point is reached, the material is maintained at the set point temperature for a five minute hold period. The first stage of heating is from 70° C. to 130° C.; the second stage of heating is from 130° C. to 160° C.; the third stage of heating is from 160° C. to 185° C.; the fourth stage of heating is from 185° C. to 205° C.; and the fifth and final stage of heating is from 205° C. to 220° C. The reaction mixture then is held at 220° C. until a Gardner-Holdt viscosity of about Z-2 is reached. This holding period typically takes about 5 hours depending on the batch size. The reaction mixture is cooled to a discharge temperature and one can then determine the physical properties of the maleated product. Typically, the maleated product exhibits an acid number (hydrous) equal to 300-320 mgKOH/g, a specific gravity of 1.04 and a Brookfield Viscosity (at 25° C.) equal to 2700-3400 cps.

To produce a maleated and oxidized fatty acid material of the present invention, the maleated tall oil fatty acid is then charged to a reactor which is fitted with an agitator, a thermocouple and a fritted glass sparge stone attached by a hose to an air supply. The maleated tall oil fatty acid is heated to 165° C. and the air is turned on and adjusted to a flow rate of 4 L/hr through the sparge stone. The reaction mixture is then heated to 177° C. and sampled frequently for acid value and viscosity (Gardner-Holdt) while holding at 177° C. The reaction mixture is held at 177° C. for 10.5-16 hours as air is sparged. The reaction mixture is then cooled to 70-85° C. and discharged. The final physical properties of the maleated and oxidized TOFA can be determined. In one example, the properties of the maleated and oxidized TOFA was measured as:

|  | Oxidized Maleated Tall Oil Fatty Acid |
|---|---|
| Acid Value | 250 |
| Density (25° C.; Lbs./gal) | 8.80 |
| Specific Gravity (25° C.) | 1.056 |
| Brookfield Viscosity (cPs; 25° C. | 17530 |

EXAMPLE 5

Several oxidized and maleated tall oil products were examined for their ability to produce oil well mud (emulsion) without the use of a nitrogen-containing secondary emulsifier. The standard emulsifier comprises a blend of a primary emulsifier which consists of a carboxylic acid source mixed with an amine source and a secondary emulsifier which is a polyamide based material. The results presented in the table indicate that acceptable emulsification is achievable in the present invention using only a single emulsifier. For purpose of comparison, proprietary tests examining fluid loss values (FL) and the electrical stability (ES) of various samples were conducted. The fluid loss values (FL) are much lower compared to the industry standard emulsifier package and the electrical stability is fairly high. This suggests that lower cost, more environmentally-friendly emulsifiers can be made using compositions of this invention.

|  | Standard Emulsifier | Maleated TOFA | Oxidized XTOL ® 690 | Oxidized Maleated TOFA | Maleated MTO | Oxidized XTOL ® 692 |
|---|---|---|---|---|---|---|
| Conc. (ppb) | 9 | 9 | 9 | 9 | 9 | 9 |
| ES | 787 | 499 | 549 | 647 | 448 | 644 |
| FL (mLs) | 6.6 | 6.0 | 3.2 | 11.6 | 3.6 | 3.4 |

EXAMPLE 6

Maleated and oxidized tall oil products of the present invention also have been tested in corrosion inhibitor formulations under both sweet gas (no $H_2S$ present) and sour gas ($H_2S$ present) conditions. Sweet gas-corrosion tests were conducted under the following conditions: Brine composition—3.3% NaCl and 1.2% $CaCl_2$; Ratio—80% brine and 20% deodorized kerosene (air blown); Gas-saturated $CO_2$; Temperature—160° F. (71° C.); Time—72 hours. The results of the sweet gas tests are listed in the Table below. The amine used in all of the tests was tall oil-based imidazoline. The samples were evaluated using the Wheel Test Method for Evaluation of Film-Persistent Corrosion Inhibitors for Oilfield Applications, Item No. 24007, NACE International Publication 1D182 (2006 Edition).

|  | % Protection | | |
|---|---|---|---|
| Samples | 5 ppm | 10 ppm | 20 ppm |
| Control A | 79 | 92 | 96 |
| Amine + Oxidized and Maleated TOFA | 96 | 97 | 97 |
| Amine + Oxidized XTOL 692 | 90 | 90 | 92 |
| Control B | 90 | 93 | 96 |
| Amine + Malaleated TOFA | 98 | 99 | 87 |
| Control C | 64 | 88 | 88 |
| Amine + Oxidized XTOL 692 | 79 | 86 | 93 |
| Amine + Maleated MTO | 85 | 84 | 88 |

For sour gas test conditions (only significant difference was that $H_2S$ was added to the test gas) the results are shown in the following table. The control was an amine (DETA/Imidazoline) neutralized TOFA. Again, the Wheel Test Method was used:

| Coupon | Wt. Loss (mg) | % Protection | Mils/Year | Sample @ ppm |
|---|---|---|---|---|
| 1 | 7.1 | 80.8 | 30.7 | Maleated TOFA @ 2500 |
| 3 | 3.3 | 91.1 | 14.2 | Maleated TOFA @ 5000 |
| 5 | 8.2 | 77.8 | 35.4 | Oxidized XTOL 690 @ 2500 |
| 7 | 4.2 | 88.6 | 18.1 | Oxidized XTOL 690 @ 5000 |
| 9 | 6.3 | 83.0 | 27.2 | Oxidized XTOL 692 @ 2500 |
| 11 | 3.0 | 91.9 | 13.0 | Oxidized XTOL 692 @ 5000 |
| 13 | 6.4 | 82.7 | 27.6 | Maleated MTO @ 2500 |
| 15 | 2.9 | 92.2 | 12.5 | Maleated MTO @ 5000 |
| 17 | 5.6 | 84.9 | 24.2 | Oxidized and Maleated TOFA @ 2500 |
| 19 | 4.4 | 88.1 | 19.0 | Oxidized and Maleated TOFA @ 5000 |
| 21 | 4.7 | 87.3 | 20.3 | Control @ 2500 |
| 23 | 4.0 | 89.2 | 17.3 | Control @ 5000 |

-continued

| Coupon | Wt. Loss (mg) | % Protection | Mils/Year | Sample @ ppm |
|---|---|---|---|---|
| 25 | 40.6 | 0 | 175.3 | Blank |
| 26 | 41.7 | 0 | 180.0 | Blank |

The results of the corrosion testing indicate that these products generally are performing better than the standards used for comparison. That is, the formulations which contain an oxidized and maleated tall oil product of the present invention usually showed a higher level of protection compared to the control. In addition, the sour gas testing was performed under conditions which did not use an amine neutralization. Therefore, the present invention is demonstrating excellent corrosion inhibition while not having to use amines in the formulation which may be of an environmental advantage and may be better economically.

The present invention has been described with reference to specific embodiments. However, this application is intended to cover those changes and substitutions that may be made by those skilled in the art without departing from the spirit and the scope of the invention. Unless otherwise specifically indicated, all percentages are by weight. Throughout the specification and in the claims the term "about" is intended to encompass + or −5% and preferably is only about + or −2%.

We Claim:

1. A composition useful for inhibiting corrosion or for use as an emulsifier in preparing invert water-in-oil emulsions comprising maleated and oxidized tall oil fatty acids, the oxidized tall oil fatty acids having crosslinks of an ether linkage between hydrocarbon chains of the oxidized tall oil fatty acids obtained by sparging air or oxygen through heated tall oil fatty acids heated to a temperature above 150 ° C. wherein the composition comprises dimers, trimers, or mixtures thereof of the maleated and oxidized tall oil fatty acids.

2. The composition of claim 1 wherein the fatty acids comprise a tall oil composition containing a tall oil rosin acid.

3. The composition of claim 1 or 2 wherein the maleated fatty acids have from about 2% to about 25% by weight of maleic anhydride, fumaric acid, acrylic acid, methacrylic acid or a mixture thereof.

4. The composition of claim 3 wherein the sparging is conducted for 10.5 to 16 hours.

5. A method for reducing corrosion associated with a metal surface comprising contacting said surface with a corrosion inhibiting amount of the composition of claim 1 or 2.

6. A method for reducing corrosion associated with a metal surface comprising contacting said surface with a corrosion inhibiting amount of the composition of claim 3.

7. A method for making an emulsion from water and an oil comprising mixing with the water and the oil an emulsifying amount of the composition of claim 1 or 2.

8. A method for making an emulsion from water and an oil comprising mixing with the water and the oil an emulsifying amount of the composition of claim 3.

9. A method of preparing a composition of claim 1 useful for inhibiting corrosion or for use as an emulsifier in preparing invert water-in-oil emulsions comprising maleating and oxidizing tall oil fatty acids, wherein the oxidizing occurs by sparging air or oxygen through heated tall oil fatty acids heated to a temperature above 150 ° C. to produce a composition comprising dimers, trimers, or mixtures thereof of the maleated and oxidized tall oil fatty acids.

10. The method of claim 9 wherein the tall oil fatty acids are reacted with from about 2% to about 25% by weight of maleic anhydride, fumaric acid, acrylic acid, methacrylic acid or a mixture thereof.

11. The method of claim 10 wherein the tall oil fatty acids comprise a tall oil composition containing a tall oil rosin acid.

12. The method of claim 10 wherein the sparging is conducted for 10.5 to 16 hours.

13. A composition useful for inhibiting corrosion or for use as an emulsifier in preparing invert water-in-oil emulsions comprising maleated and oxidized tall oil fatty acids, the oxidized tall oil fatty acids having crosslinks of an ether linkage between hydrocarbon chains of the oxidized tall oil fatty acids obtained by sparging air or oxygen through heated tall oil fatty acids heated to a temperature above 150 ° C. wherein the omposition comprises one or more of the following structures:

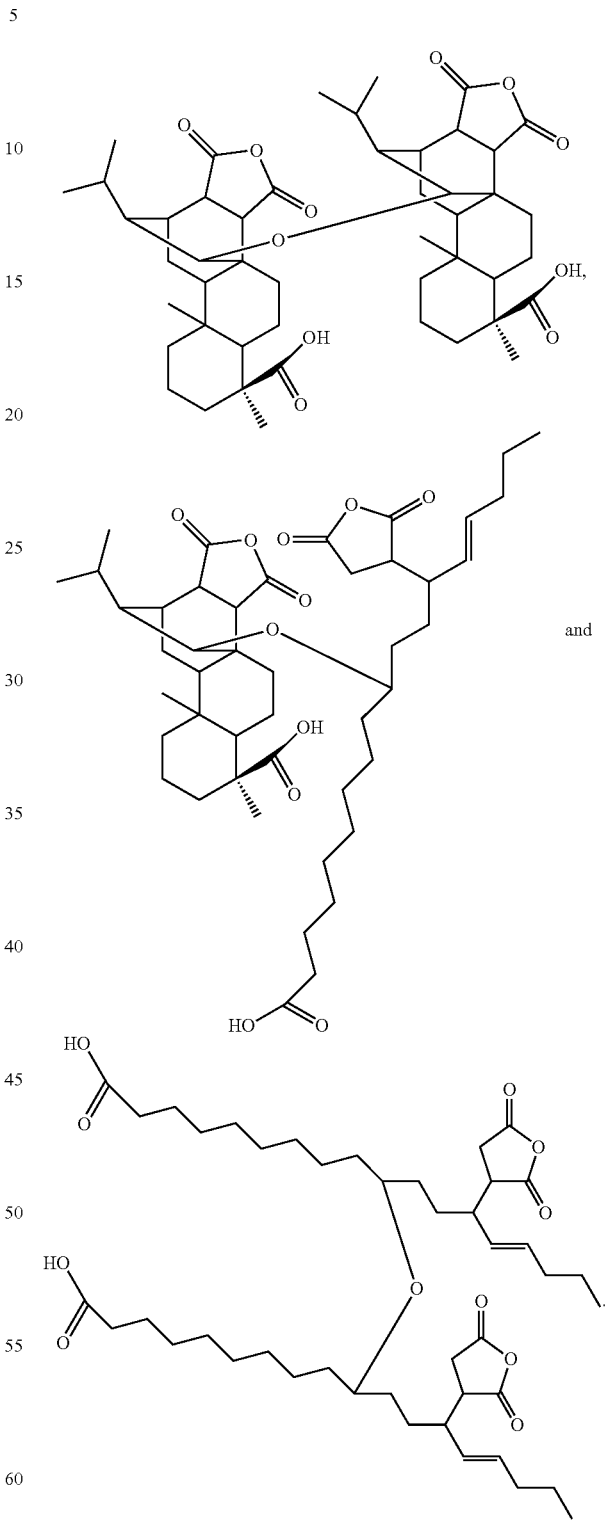

* * * * *